(12) United States Patent
Mueller et al.

(10) Patent No.: US 7,224,449 B2
(45) Date of Patent: May 29, 2007

(54) OPTICAL FLUIDIC SYSTEM WITH A CAPILLARY HAVING A DRILLED THROUGH HOLE

(75) Inventors: Beno Mueller, Ettlingen (DE); Christian Buettner, Waldbronn (DE)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 11/255,541

(22) Filed: Oct. 21, 2005

(65) Prior Publication Data

US 2007/0091304 A1    Apr. 26, 2007

(51) Int. Cl.
*G01N 21/00* (2006.01)
(52) U.S. Cl. .................................. 356/244
(58) Field of Classification Search ............. None
See application file for complete search history.

(56) References Cited

U.S. PATENT DOCUMENTS 4,710,021 A * 12/1987 von Behrens ............... 356/72
6,887,431 B1 * 5/2005 Vann et al. ................. 422/100
2003/0077027 A1 * 4/2003 Schiaffino et al. ........... 385/18

FOREIGN PATENT DOCUMENTS

JP        05196565 A  *  8/1993

* cited by examiner

*Primary Examiner*—Tu T. Nguyen

(57) ABSTRACT

A fluidic system is provided which is adapted to perform optical analysis of a fluid. The system comprises a first capillary, at least one waveguide which is adapted to guide light and at least one second capillary. The first capillary comprises at least one first opening for receiving an end of the at least one first waveguide and it comprises furthermore at least one second opening for receiving a first end of the at least one second capillary, whereby a fluid communication between the first and the second capillaries is provided. The end of the at least one waveguide is arranged to emit light into the at least one second capillary.

15 Claims, 2 Drawing Sheets

OPTICAL FLUIDIC SYSTEM WITH A CAPILLARY HAVING A DRILLED THROUGH HOLE

BACKGROUND ART

1. Field of the Invention

The present invention relates to an optical fluidic system.

2. Discussion of the Background Art

One may wish to subject fluids to light for several reasons. Two of which are the following: performance of photochemical reactions and the performance of optical detection.

Photochemical reactions may include photo polymerization or photochemical cleavage of molecules in smaller units. Both are well described in the literature and the applications are usually performed in devices having pilot plant size or technical size.

Optical detection of fluidic samples succeeding to chemical separation or preparation is a most preferred technique due to characteristics of being applicable without interfering in the chemical system being in the focus. In order to perform such optical detection generally a measuring chamber for the reception of the fluid, a light emitting and a light receiving device are needed. Performing online detection means designing a measuring chamber as a flow through cell. One may perform transmission or absorption measurements which are corresponding as indicated by optical laws such as Beer's law, which is known to those skilled in the art. Whichever technique is chosen, it presumes guiding light through the sample, accordingly a light path between a light emitting and a light receiving means is provided. Simplified, light emitting and light receiving means comprise a light source, detector and the corresponding waveguides. Applying Beer's law furthermore means knowing precisely the geometrical dimensions of the measuring device as far as they are needed to determine optical coefficients such as e.g. extinction.

Online detection is advantageously performed in a detection system which prevents turbulences followed by mixing of the sample due to dead volumes or changes of the cross sectional area of the fluid conducting device. The reliability on measuring results is based on providing a disturbance free fluid flow, allowing to measure variations of the fluid composition with the time. Performing optical detection techniques with devices designed for micro fluidic applications is still challenging since the advantage of needing only micro volumes of sample is accompanied by an increased request on the design, which should be adapted to the specific pressure and flow through characteristics, only to name some of the relevant parameters.

A device for microfluidic optical detections is described in U.S. Pat. No. 6,281,975, to Munk. He describes a capillary flow cell with protruding bulb ends providing a high light throughput entrance window for the cell, aiming for an improved sample illumination.

EP 0,089,157 to Le Febre discloses an optical detector cell for determining the presence of a solute in a sample fluid, for the particular application in miniature chromatographic and micro spectroscopic applications. An optical flow path which is parallel to the fluid flow path is provided, allowing maximizing of the sample corresponding to a fixed sample volume, whereby the ability results to measure low threshold concentrations in solutes.

U.S. Pat. No. 4,477,186 to Carlson refers to a photometric cuvette for optical analysis of through flowing media, designed for the measurement of minimum sample amounts.

SUMMARY OF THE INVENTION

It is an object of the invention to provide an improved optical fluidic system. The object is solved by the independent claim. Preferred embodiments are shown by the dependent claims.

According to an embodiment of the present invention, the fluidic system comprises an arrangement of two capillaries and a waveguide. The first one of said capillaries has two openings facing each other, one of which being adapted to receive an end of said waveguide and the second opening being adapted to receive an end of the second capillary, whereby a fluidic communication between the capillaries is provided. The waveguide that is inserted into the first capillary is furthermore arranged in a way that it emits light into or receives light from the second capillary.

A further embodiment of the invention refers to the above first embodiment, being an extended or further developed version: It comprises a third capillary and a second waveguide wherein said third capillary is designed analogously to the first one, and wherein the above depicted second capillary serves as linking element between the first and the third capillary, whereby an "H"-shaped optical fluidic system is designed. The first and the third capillary correspond optically and fluidic via the second capillary with each other. The interface of the first and second waveguides and the location of the second capillary between the first and the third one is designed advantageously in a way that performance of optical analysis of a flowing fluid as well as subjecting of a flowing fluid to light is permitted under avoidance of dead volumes in the system. In case of detection this means reduction of smearing of compounds being comprised in a cross sectional area of the flowing fluid into a later measuring time interval whereby an increased reliability on the measuring results is obtained.

BRIEF DESCRIPTION OF THE DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

DETAILED DESCRIPTION OF THE PREFERRED EMBODIMENT

Optical detection of a fluid may generally be carried out by drawing a sample, which is a fluidic sample herein, from a sample source, conducting it along an optical measuring path and then into a sample sink. The "drawing" could be simply mean bypassing of a certain amount of sample fluid during an ongoing process, and a "sink" may be a sample waste, accordingly the sample is removed of the system, then. Or the "sink" could be the same container where the sample was drawn from, actually recycling of the sample is achieved and, hence, is proceeded in the still ongoing process when it is flowing back in said container. Another option is, that one could select a different device as "sink", which is adapted to carry out further processing of the fluid. The embodiments of the present invention disclose optical fluidic detection systems which permit recycling of the sample fluid as well as conducting it to further processing or dismissing it.

Figure 1:
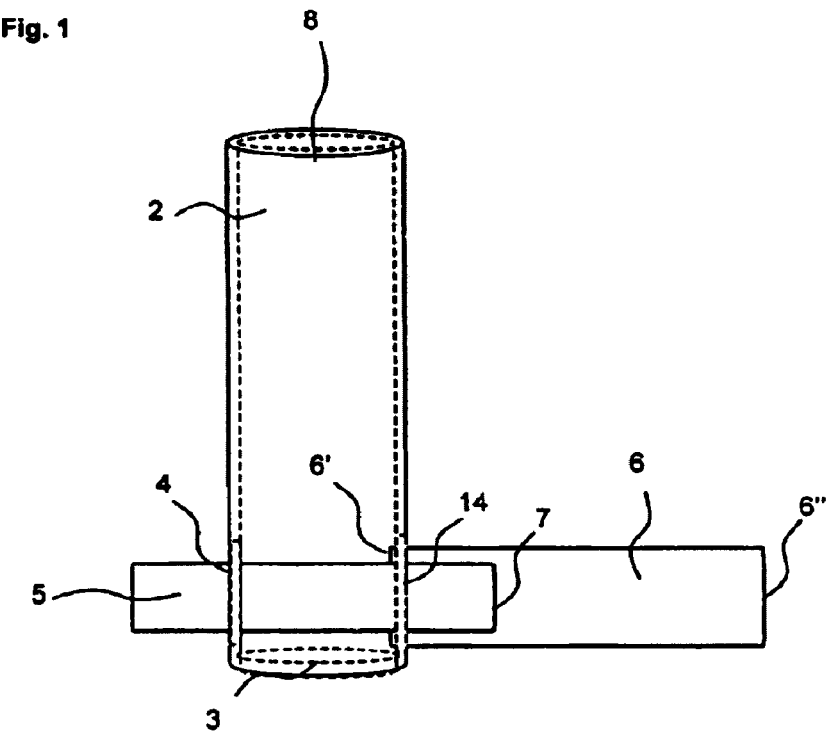
FIG. 1 shows the first capillary being in optical and fluidic communication with the second capillary.

FIG. 1 shows a first simple embodiment of the present invention which could be used as well for performance of photochemical reactions as for the performance of optical detection. The herein shown system comprises a first capillary 2, a first waveguide 5 and a second capillary 6. The first capillary 2 has a first opening 4, which is designed to receive the waveguide 5, or the end 7 of said waveguide, respectively. The second opening 14, which is located opposite to the first opening 4, is designed to receive a first end 6' of said second capillary 6. Inside the first capillary 2 the first waveguide 5 is inserted into the second capillary 6, accordingly the diameter of that second opening 14 is larger than the diameter of the first opening 4. Since the diameter of the waveguide 5 is smaller than the diameter of the second capillary 6, an annular gap 15 is provided around the waveguide 5 inside said second capillary 6 and, hence, a fluid may flow from the first capillary into the second capillary. Since the end 7 of the first waveguide 7 is inserted into said second capillary 6, it may emit light into the second capillary 6.

Other embodiments could be designed arranging the first and the second capillaries in other suitable geometric relations to each other, so the orthogonal arranged embodiment shown in FIG. 1 is not intended to be limited.

Another option is that said waveguide 7 could receive light in case it faces a light source which is arranged inside or behind said second capillary 6. So, the herein shown system is adapted to perform optical analysis of a fluid as well as it may be operated to subject a fluid to light in order to perform a photo reaction. In both cases the fluid is injected into the first capillary 2 via the inlet 8, and then it flows via into the second capillary 6 into a "sink" which is not shown in FIG. 1.

By closing of the capillary 2, a bottom end 3 is provided. So, the orthogonal arrangement of the first and the second capillaries 2,6 and of the waveguide 5 is located close to the bottom end 3 of the first capillary 2, which results in a design offering minimized dead volumes, whereby advantageously collecting of fluid inside the first capillary 2 below the waveguide 5 is avoided. This prevents retaining of sample fluid in "dead ends", which sample fluid would otherwise be detected with a postponement; thereby the reliability of the measurement results might be affected.

As indicated by using of the word "capillary" for the fluid conducting device, the fluidic system of the embodiments described herein could advantageously be operated for carrying out microfluidics.

Figure 3:
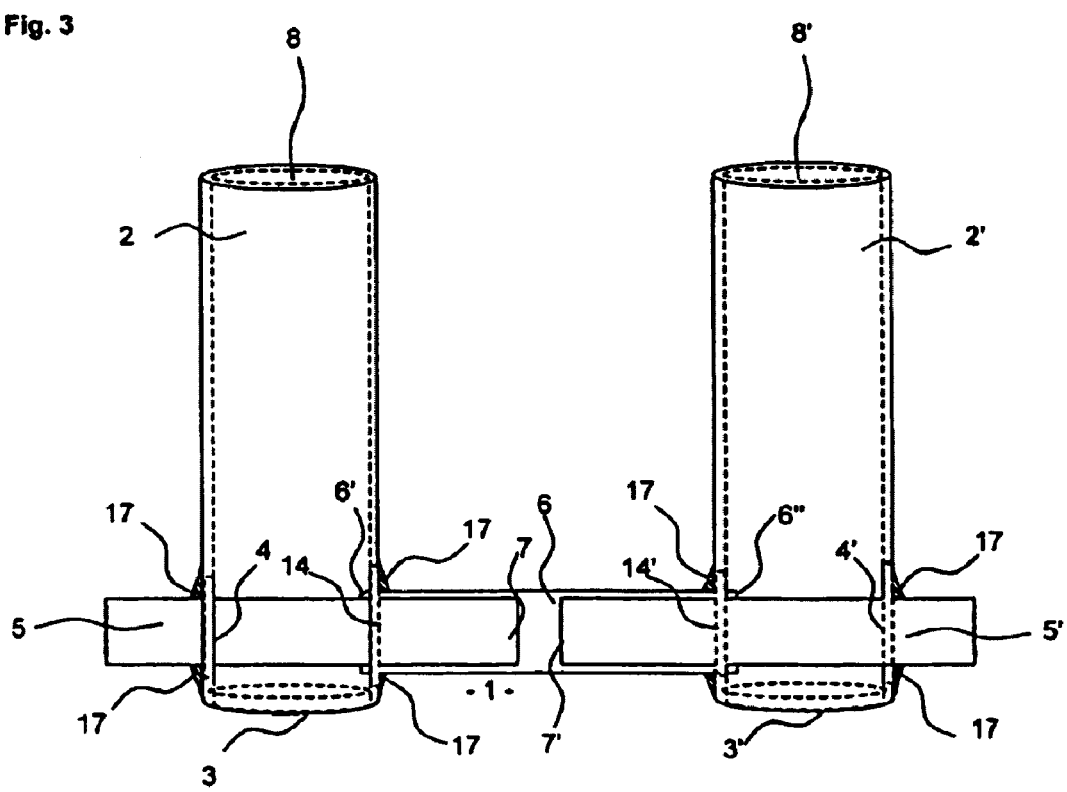
FIG. 3 shows the device of FIG. 2, depicting the welding seams being generated by quartz welding.

In FIG. 3, an extended or further developed version of the system shown in FIG. 1 is illustrated. Herein, the first capillary 2 is in fluidic communication with a third capillary 2', with the second capillary 6 serving as linking device a and partial light path. Said third capillary 2' is designed reverse to the first capillary 2. Accordingly is has two first and second openings 4',14', an opening 8' and a closed bottom 3'. It comprises a second waveguide 5', which is adapted to guide light, too. It is arranged in mirror-image position to the first capillary 2; its first opening 4' is designed for receiving a first end 7' of the second waveguide 5', whereas its second opening 14', which faces said first opening 4', receives a second end 6" of the second capillary 2'. Accordingly, a fluidic communication is provided between the first, second and the third capillaries 2,6,2'.

Figure 2:
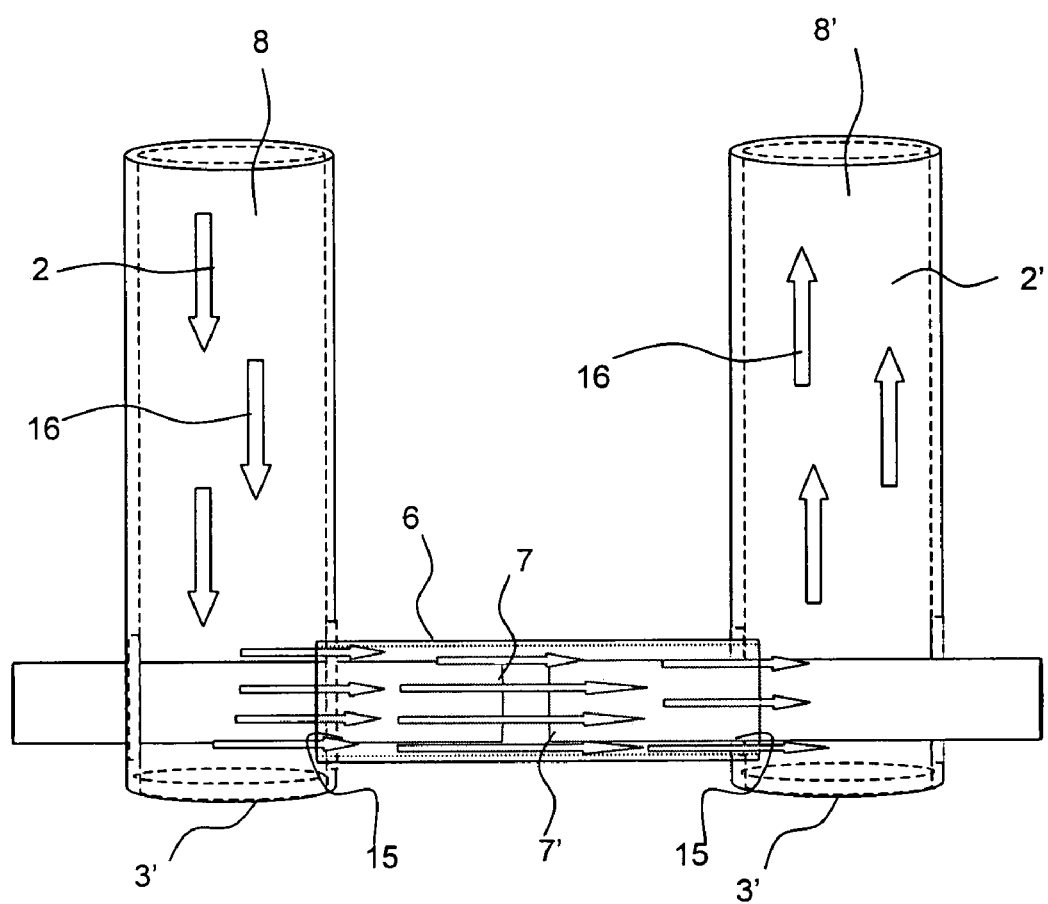
FIG. 2 shows the first capillary being in fluidic communication with the third capillary, with the second capillary serving as linking device and light path.

As can be seen in FIG. 2, the optical fluidic device could be operated as flow-through system with the opening 8' of the third capillary 2' being an outlet when the opening 8 of the second capillary 2 is operated as inlet. The fluid is injected into the system via the inlet 8 of the first capillary 2, then it flows into the second capillary 6, passing a first annular gap 15 which is provided between the first waveguide 5 and the second capillary 6. Passing a second annular gap 15', it enters the third capillary 2', which it may leave via the outlet 8'.

Depending on the operating mode of the optical fluidic system, the waveguides 5, 5' may be facing each other within said second capillary in a long or a short distance. When the system is operated in order to perform optical detection the distance between the ends 7, 7' of the waveguides 5,5' can be set in accordance to the fluid and the fluid components which are intended to be detected.

One might wish to integrate two or more second capillaries between the first and third capillary to provide optical measuring paths having different lengths and, hence, having different distances between the ends of the emitting and receiving waveguides, in order to focus on different component concentrations in the fluid. Different concentrations may according to the law of Beer, e.g., be detected with an improved precision and reliability when the optical measuring path is adapted to the concentration of the substance to be measured: Highly concentrated components could advantageously be detected by use of short measuring paths, whereas low concentrations could be detected by use of long measuring paths. The different lengths of the measuring paths are achieved by the immersion depth of the emitting and/or receiving waveguides into the second capillaries.

Another option to realize the before principle of measuring different concentrations by use of different measuring path lengths is the providing of one first capillary, being the supplying capillary with respect to the injected fluid, and two or more second capillaries serving as measuring devices and having different optical measuring paths in the before sense, each of which second capillaries being connected to a third capillary serving to remove the measured fluid. The "removing" third capillary could be one single capillary, as depicted before, or a plurality of third capillaries, whereby each one of the second capillaries is connected to one of the third capillaries.

Generally, the first and the second waveguides may have complementary functions in case they are operating parts of an optical measuring device. Then, one of the waveguides might serve as light emitting and the other one might serve as light receiving device. In case the optical fluidic device is used to perform photochemical reactions, one could use both waveguides as light emitting devices.

Advantageously, fluidic system of the above depicted embodiments is made of quartz components, accordingly capillaries and the waveguides are generally made of quartz. This permits firstly to provide the closing of the bottom ends of the first and third capillaries by sealing them off, and, secondly, it allows to perform the following sealing techniques where it is necessary:

The fluidic system comprises a plurality of openings such as the first and second openings 4,14 of the first capillary, which were depicted in FIGS. 1 to 3, and the first and second openings 4',14' of the third capillary, which were depicted in FIGS. 2 and 3. The first openings 4,4' are serving to receive the first and second waveguides 5,5', whereas the second openings 14,14' are serving to receive the second capillary.

So, a number of interconnections is provided which advantageously should be sealed tightly in order to allow operating of the system at pressures in a range of 200 to 1000 bar.

These interconnections might be sealed using the following techniques:

one could provide a sealing in that quartz welding is performed by heating up the first and/or second capillaries and the third and/or second capillaries to melting temperature in the regions around said interconnections. The melting quartz becomes highly viscous and, hence, flows into the spaces provided between the first openings 4,4' and the waveguides 5,5' and the second openings 14,14' of the first and third capillaries 2,2' and the second capillary.

Additionally or optionally one might ad a volume of extra quartz melt at said interconnection regions, whereby a welding seam 17 could be generated, as shown in FIG. 3.

An additional option to provide an interconnection which is sealed tightly could be the application of a gluing material or, respectively, adhesive material. Gluing materials could be polymeric substances such as epoxy adhesive materials or polyetherketones, in particular polyetheretherketone or any other suitable polyetherketone. This polymeric material could be added in and around the openings 4,4',14,14' in a fluidic state, thus it may flow into the gaps. Hardening or curing of the material provides a pressure proof sealing.

In order to stabilize the fluidic system of the embodiments of the present invention, one could embed the system partially or completely in quartz. A quartz bed would provide an advantageous stabilization of fragile components such as capillaries and waveguides. Using quartz for the embedding would allow the components to extend thermally since the embedding material and the fluidic system material have the same thermal extension coefficients.

What is claimed is:

1. A fluidic system adapted to subject a fluid to light, comprising:
    a first capillary,
    at least one first waveguide adapted to guide light, and
    at least one second capillary,
   wherein:
    the first capillary comprises at least one first opening for receiving an end of the at least one first waveguide,
    the first capillary comprises at least one second opening for receiving a first end of the at least one second capillary, thus providing a fluid communication between the first and the second capillaries, and
    the end of the at least one first waveguide can emit light into the at least one second capillary or receive light from the at least one second capillary.

2. The fluidic system of claim 1, comprising at least one third capillary which comprises:
    at least one second waveguide adapted to guide light,
   wherein:
    the at least one third capillary comprises at least one first opening for receiving an end of the at least one second waveguide,
    the at least one third capillary comprises at least one second opening for receiving a second end of the at least one second capillary, thus providing a fluid communication between the second and the third capillaries, and
    the end of the at least one second waveguide is arranged to receive light emitted from the at least one first waveguide.

3. The fluidic system of claim 2, wherein the at least one third capillary comprises:
    an inlet-end, a side-wall and a closed bottom-end and wherein:
    said first and second openings are comprised in the side-wall, wherein each first opening faces one of said second openings and with the first and second openings being located close to the bottom-end.

4. The fluidic system of claim 2, wherein:
    the end of the at least one first waveguide is inserted into said at least one second capillary via said first and second openings of the first capillary and
    the end of the at least one second waveguide is inserted into said at least one second capillary via said first and second openings of the at least one third capillary,
   whereby optical communication between the first and second waveguides within the at least one second capillary is provided.

5. The fluidic system of claim 4, wherein each second capillary provides an optical measuring path with a measuring path length, which measuring path length is determined by an insertion depth of the first and second waveguides into said at least one second capillary.

6. The fluidic system of claim 4, wherein:
    a first annular gap is provided between the at least one first waveguide and the at least one second capillary and
    a second annular gap is provided between the at least one second waveguide and the at least one second capillary, whereby a fluidic communication is provided between said first, second and third capillaries.

7. The fluidic system of claim 2, wherein:
    said first, second and third capillaries and the first and second waveguides are made of quartz.

8. The fluidic system of claim 7, wherein a sealing is provided between at least one of:
    the at least one first opening of the first capillary and the at least one first waveguide,
    the at least one first opening of the at least one third capillary and the at least one second waveguide,
    the at least one second opening of the first capillary and the at least one second capillary, and
    the at least one second opening of the at least one third capillary and the at least one second capillary,
   in that a quartz welding is performed by heating up at least one of the first and second capillaries and at least one of the third and second capillaries to melting temperature in a region adjacent to said first and second openings.

9. The fluidic system of claim 7, wherein a sealing is provided between at least one of:
    the at least one first opening of the first capillary and the at least one first waveguide,
    the at least one first opening of the at least one third capillary and the at least one second waveguide,
    the at least one second opening of the first capillary and the at least one second capillary, and
    the at least one second opening of the at least one third capillary and the at least one second capillary,
   in that a volume of extra quartz melt is added in a region adjacent to said first and second openings.

10. The fluidic system of claim 2, wherein at least one of
    the at least one first opening of the first capillary and the at least one first waveguide,
    the at least one first opening of the at least one third capillary and the at least one second waveguide,
    the at least one second opening of the first capillary and the at least one second capillary, or
    the at least one second opening of the at least one third capillary and the at least one second capillary are joined by fitting a material being one of a polymeric adhesive material such as an epoxy adhesive material, a polyetherketone, in particular polyetheretherketone or any other suitable polyetherketone, in said first and second openings, providing a joint due to molding.

11. The fluidic system of claim 2, wherein the fluidic system it is embedded in a quartz bed.

12. The fluidic system of claim 1, wherein the first capillary comprises:
  an inlet-end, a side-wall and a closed bottom-end and wherein:
said first and second openings are comprised in the side-wall, wherein each first opening faces one of said second openings and with the first and second openings being located close to the bottom-end.

13. The fluidic system of claims 12, wherein the closed bottom end is provided by sealing off the capillary.

14. The fluidic system of claim 1, wherein said first waveguide protrudes through said first opening and said second opening.

15. The fluidic system of claim 14, wherein said first waveguide protrudes into said second capillary, so that said fluid passes over an end of said waveguide that is disposed within said second capillary.

* * * * *